(12) United States Patent
Roberts et al.

(10) Patent No.: US 8,135,469 B2
(45) Date of Patent: Mar. 13, 2012

(54) ENERGY HARVESTER FOR AN IMPLANT DEVICE

(75) Inventors: Stephen Roberts, Winchester (GB); Roy Freeland, Shawford (GB); Giles Stanley, Chandlers Ford (GB); Keith Dobson Dawkins, Boston, MA (US); John Mark Morgan, Houghton (GB); Paul R. Roberts, Southampton (GB)

(73) Assignee: Perpetuum Ltd., Chilworth Science Park, Southampton (GB)

( * ) Notice: Subject to any disclaimer, the term of this patent is extended or adjusted under 35 U.S.C. 154(b) by 623 days.

(21) Appl. No.: 12/041,298

(22) Filed: Mar. 3, 2008

(65) Prior Publication Data

US 2008/0262562 A1    Oct. 23, 2008

(30) Foreign Application Priority Data

Apr. 17, 2007 (GB) .................... 0707388.5
Jul. 4, 2007 (GB) .................... 0712979.4

(51) Int. Cl.
*A61N 1/362* (2006.01)
(52) U.S. Cl. ........................................... 607/35
(58) Field of Classification Search ............ 607/35
See application file for complete search history.

(56) References Cited

U.S. PATENT DOCUMENTS

| | | | |
|---|---|---|---|
| 3,563,245 A * | 2/1971 | McLean et al. ............. | 607/35 |
| 3,693,625 A * | 9/1972 | Auphan ..................... | 607/19 |
| 3,826,265 A | 7/1974 | Giori et al. | |
| 4,245,640 A | 1/1981 | Hunt | |
| 4,763,646 A * | 8/1988 | Lekholm ..................... | 607/14 |
| 2003/0168861 A1 | 9/2003 | Estevez | |
| 2004/0021322 A1 | 2/2004 | Ariav | |
| 2004/0088012 A1* | 5/2004 | Kroll et al. ................. | 607/9 |
| 2004/0116981 A1* | 6/2004 | Mazar ....................... | 607/60 |
| 2004/0230129 A1* | 11/2004 | Haefner ..................... | 600/510 |
| 2004/0230255 A1* | 11/2004 | Dobak, III ................. | 607/58 |
| 2005/0256549 A1* | 11/2005 | Holzer ....................... | 607/35 |
| 2006/0184206 A1 | 8/2006 | Baker, III et al. | |
| 2006/0235289 A1* | 10/2006 | Wesselink et al. ......... | 600/407 |
| 2007/0088402 A1 | 4/2007 | Melvin | |
| 2007/0219591 A1* | 9/2007 | Zdeblick et al. ............ | 607/17 |
| 2007/0276444 A1 | 11/2007 | Gelbart et al. | |

FOREIGN PATENT DOCUMENTS

DE   10-2004-043-002 A1   3/2006

(Continued)

OTHER PUBLICATIONS

UK Intellectual Property Office Search Report dated Aug. 21, 2007 for Application No. GB0707388.5.

(Continued)

*Primary Examiner* — Carl H Layno
*Assistant Examiner* — Paula J Stice
(74) *Attorney, Agent, or Firm* — Colin P. Cahoon; Celina M. Orr; Carstens & Cahoon, LLP

(57) ABSTRACT

This invention relates to the use of an electromagnetic generator and a pressure bladder located within a biological body in such a position to take advantage of the pressure fluctuations found within that body to produce electrical power. The invention uses these pressure fluctuations to displace the moving parts of a generator, to produce electricity in accordance with the Faraday principal, to power implanted devices.

65 Claims, 3 Drawing Sheets

FOREIGN PATENT DOCUMENTS

| | | |
|---|---|---|
| GB | 1220677 | 1/1971 |
| GB | 1281646 A | 7/1972 |
| GB | 2350302 A | 11/2000 |
| WO | 99/13940 A1 | 3/1999 |
| WO | 00/25860 A | 5/2000 |
| WO | 00/78376 A1 | 12/2000 |
| WO | 2004/032788 A2 | 4/2004 |
| WO | 2006088696 A2 | 8/2006 |
| WO | 2007/090023 A1 | 8/2007 |
| WO | 2007/149462 A | 12/2007 |

OTHER PUBLICATIONS

International Search Report dated Aug. 21, 2008 for Application No. PCT/GB2008/001342.

International Search Report dated Aug. 12, 2008 for Application No. GB0712979.4.

* cited by examiner

ENERGY HARVESTER FOR AN IMPLANT DEVICE

BACKGROUND OF THE INVENTION

1. Field of the Invention

The present invention relates generally an energy harvester for an implant device and to an implant device including such an energy harvester. The present invention also relates to an implant apparatus for implantation into a mammal, a method of implanting an implant apparatus into a mammal and a method of operating an implant apparatus that is implanted into a mammal. In particular, the present invention relates generally to the field of power generation within a biological living body, such as a mammal, using motions of that body to produce electrical energy, to power a variety of types of implant devices.

2. Description of the Prior Art

Current medical implant devices, such as pacemakers and defibrillators, rely heavily on electrical power to function for extended periods of time. However, current battery technology is the principal limiting factor to the life span of these devices, as battery capacity has reached a plateau, with recent developments in battery technology producing only marginal increases in storage capacity to volume ratios.

Some implanted devices are able to be recharged through the use of induction loops implanted subcutaneously. By coupling an implanted loop to an external induction re-charger, an implanted device can be recharged to extend it operational life. This, however, requires the patient to monitor the power levels of the implanted device and to position the induction re-charger at regular intervals, to ensure the device is kept charged.

Not only is this time consuming for the patient, but is also inefficient in its power use, as a large proportion of the energy used to power the induction loop is lost due to heating and magnetic field fringe effects. Inefficiencies are also experienced by misalignment of the two induction loops, reducing the coupling efficiency of the power transmission.

This technique can also produce levels of psychological stress within the patient, with regards to the anxiety of a power failure of the implanted device.

It has been thought that an implantable generator, which uses motions of the body to produce power for implanted devices, would be of significant interest to the medical implant industry and so of commercial value to the entity that could produce such a generator.

US-A-2005/0256549 discloses a micro-generator implant device including (a) a micro-generator, disposed within a living body, the micro-generator including: (i) a first mechanism for harnessing mechanical energy from a natural body movement, and (ii) a second mechanism for converting the mechanical energy to electrical energy, the electrical energy for providing power within the living body. In particular, this specification discloses a great many energy harvesting techniques, employing (a) motion of heart muscle tissue; (b) motion of blood passing through a blood vessel; or (c) motion of a limb, or of the entire body as the source of mechanical energy. All of these proposals suffer from the problems of technical complexity and/or the requirement for an invasive surgical procedure and/or long term reliability and/or the possibility of secondary medical problems. For example, the use of the motion of blood passing through a blood vessel requires a complicated rotating mechanism, namely a "watch mechanism", to be implanted into an artery.

The present invention aims at least partly to overcome these problems of the known implant devices and the energy source therefor.

SUMMARY OF THE INVENTION

Accordingly, the present invention provides an energy harvester for an implant device, the energy harvester comprising a pressure responsive device containing a working fluid, and an electrical generator which is coupled to the pressure responsive device and is adapted to convert pressure changes in the working fluid into electrical energy.

The present invention further provides an implant device including the energy harvester according to the present invention.

The implant device may be selected from a cardiac defibrillator or a cardiac pacemaker in its preferred embodiment. Other implants that could benefit from this technology will be apparent to those skilled in the art.

The present invention yet further provides an implant apparatus for implantation into a mammal, the implant apparatus comprising:

an implant device having an electrode lead for implantation into the heart;

an energy harvester comprising a pressure responsive device for containing a working fluid, and an electrical generator which is coupled to the pressure responsive device and is adapted, in use, to convert pressure changes in the working fluid into electrical energy; and at least one electrical connection between the electrical generator and the implant device, the electrical generator being adapted to provide electrical power to the implant device.

The present invention yet further provides a method of implanting an implant apparatus into a mammal, the method comprising the steps of:

(a) providing an implant apparatus comprising:

an implant device having an electrode lead for implantation into the heart;

an energy harvester comprising a pressure responsive device for containing a working fluid, and an electrical generator which is coupled to the pressure responsive device and is adapted, in use, to convert pressure changes in the working fluid into electrical energy; and at least one electrical connection between the electrical generator and the implant device, the electrical generator being adapted to provide electrical power to the implant device; and (b) implanting at least a part of the pressure responsive device and the electrode lead into the heart in a common catheterisation step.

The present invention also provides an implant apparatus for implantation into a mammal, the implant apparatus comprising:

an implant device having an electrode lead for implantation into the heart;

an energy harvester comprising a pressure responsive device for containing a working fluid, and an electrical generator which is coupled to the pressure responsive device and is adapted, in use, to convert pressure changes in the working fluid into electrical energy; and at least one electrical connection between the electrical generator and the implant device, the electrical generator being adapted to provide electrical power to the implant device and a signal feed output to be processed by the implant device.

The present invention yet further provides an implant device for implantation into a mammal, the implant device comprising:

a cardiac device having an electrode lead for implantation into the heart;

an energy harvester comprising a pressure responsive device for containing a working fluid, and an electrical generator which is coupled to the pressure responsive device and is adapted, in use, to convert pressure changes in the working fluid into electrical energy;

at least one electrical connection between the electrical generator and the implant device, the electrical generator being adapted to provide electrical power to the implant device and a signal feed output to be processed by the implant device; and at least one sensor associated with the electrode lead, the at least one sensor being adapted to monitor at least one parameter of a patient's blood biochemistry.

The present invention further provides an implant device for implantation into a mammal, the implant device comprising: a pressure responsive device for containing a working fluid, and an electrical generator which is coupled to the pressure responsive device and is adapted, in use, to convert pressure changes in the working fluid into electrical energy and to output a signal that is representative of pressure changes within the body of the mammal.

Preferably, the implant device further comprises a cardiac device having an electrode lead for implantation into the heart; at least one electrical connection between the electrical generator and the implant device, the electrical generator being adapted to provide electrical power to the implant device, and wherein the cardiac device is adapted to receive the signal.

More preferably, the cardiac device is adapted to derive and store data from the signal within the cardiac device. The cardiac device may be adapted to permit the stored data to be downloaded therefrom to a remote device.

The present invention also provides a clinical apparatus comprising the implant device according to the present invention in combination with a processor adapted to receive and process the signal to provide clinical data.

The clinical data may comprise information on at least one of right atrial and right ventricular function of the heart of a subject, and/or information on cardiac arrhythmias.

The processor may be adapted to store the clinical data over a period of time to record trend data to provide a measure of disease progression. The processor may be adapted to provide a feedback control signal, based on the clinical data, for the implant device.

The present invention yet further provides a method of operating an implant apparatus that is implanted into a mammal, the implant apparatus having a pressure responsive device for containing a working fluid, and an electrical generator which is coupled to the pressure responsive device and is adapted, in use, to convert pressure changes in the working fluid into electrical energy and to output a signal that is representative of pressure changes within the body of the mammal, the method including:

processing a signal output from the electrical generator that is representative of the pressure changes within the body of the mammal to determine a physiological condition of the body.

The signal output from the electrical generator may be representative of combined cardiac haemodynamic-rhythm perturbation.

Preferably, the processing step provides clinical data from the signal output. The clinical data may comprise information on at least one of right atrial and right ventricular function of the heart of the mammal and/or information on cardiac arrhythmias.

The processing step may store the clinical data over a period of time to record trend data to provide a measure of disease progression. The processing step may provide a feedback control signal, based on the clinical data, for the implant apparatus.

The implant apparatus may comprise a cardiac device including an electrode lead implanted into the heart, and at least one electrical connection between the electrical generator and the cardiac device, the electrical generator providing electrical power to the implant device In general, the present invention concerns the physical construction and the potential applications of a body powered energy harvester, principally intended to power implantable medical devices such as pacemakers and defibrillators, although the body powered energy harvester could alternatively be used to power other medical or non-medical implantable devices.

In a particularly preferred embodiment, the present invention relates to the use of an electromagnetic generator and a pressure bladder located within a biological living body, in a particular a mammal, such as the human body, in such a position to take advantage of the pressure fluctuations found within that body to produce electrical power. The energy harvester implant device of the present invention uses these pressure fluctuations to displace the moving parts of an electromagnetic generator, to produce electricity in accordance with the Faraday principle, to power implanted devices.

The present invention yet further provides an implant apparatus for implantation into a mammal, the implant apparatus comprising: a pressure responsive device for containing a working fluid, and an electrical generator which is coupled to the pressure responsive device and is adapted, in use, to convert pressure changes in the working fluid into electrical energy; the pressure responsive device comprising at least two pressure-deformable portions and a pressure transmission conduit therebetween.

BRIEF DESCRIPTION OF THE DRAWINGS

Embodiments of the present invention will now be described by way of example only, with reference to the accompanying drawings, in which.

DETAILED DESCRIPTION OF THE PREFERRED EMBODIMENTS

Figure 1:
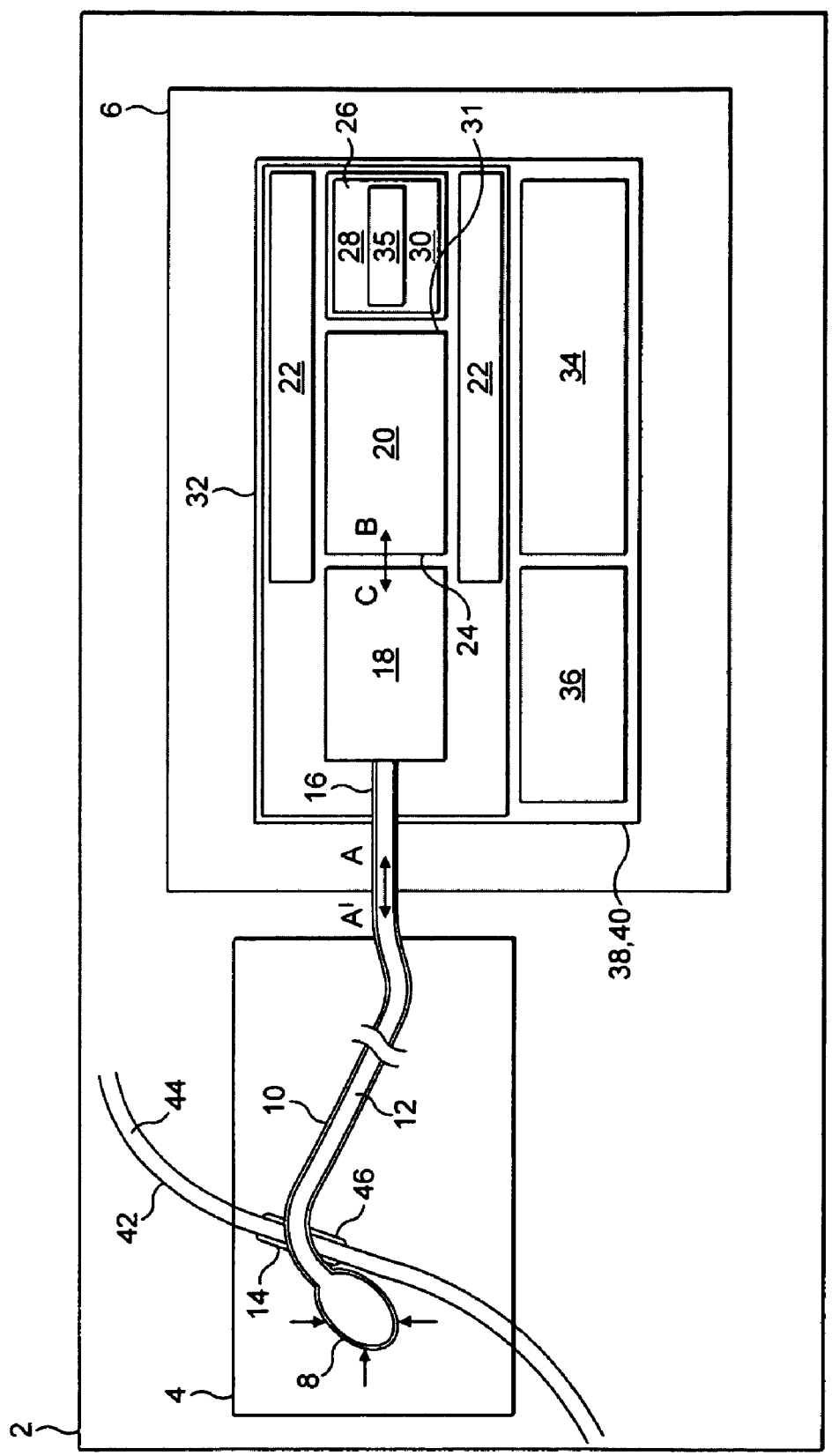
FIG. 1 is a schematic diagram of an energy harvester implant device in accordance with a first embodiment of the present invention.

Referring to FIG. 1, there is shown schematically an energy harvester implant device in accordance with a first preferred embodiment of the present invention when implanted into the human body.

The energy harvester implant device, designated generally as 2, comprises a pressure responsive device 4 containing a working fluid coupled to an electrical generator 6 which converts pressure changes in the working fluid into electrical energy. In use, the energy harvester implant device 2 is implanted into the living body so that the pressure responsive device 4 is subjected to pressure fluctuations within the living body, and in particular to blood pressure fluctuations found within the blood circulatory system.

The pressure responsive device 4 comprises a deformable pressure bladder 8 and a pressure transmission conduit 10. The pressure responsive device 4 is a hydraulic or pneumatic device, and is filled with a pressure transmitting working fluid 12 which is a biologically inert liquid or gas. The pressure bladder 8, which may comprise a bellows structure, is located at one end 14 of the pressure transmission conduit 10 and the other end 16 of the pressure transmission conduit 10 is located within the electrical generator 6. The pressure transmitting working fluid 12 is caused selectively to move along the conduit 10 in opposed directions, dependent on the pressure drop along the conduit 10, shown by the arrows A and A', and thereby to transmit the pressure fluctuations found within the circulatory system, detected by the pressure bladder 8, to the electrical generator 6. Such pressure fluctuations are periodic. For example, in a compression phase of a power generation cycle, when the pressure bladder 8 is compressed by relatively high blood pressure, the working fluid 12 is passed, under hydraulic or pneumatic pressure, along the conduit 10, connecting the pressure bladder 8 to the electrical generator 6. Once within the generator 6, the working fluid 12 is directed into an expansion mechanism 18, which operates to generate electrical power as discussed in detail below. In a return phase of the power generation cycle, when the blood pressure on the bladder 8 is relatively low, the working fluid 12 returns to the bladder 8 from the expansion mechanism 18 under the influence of pressure equalisation.

The expansion mechanism 18 is connected to at least one moving component 20 of the electrical generator 6. The at least one moving component 20 is a magnet, a conductive coil or a magnetically permeable material, which is disposed in such a position so as to be electromagnetically coupled to at least one stationary component 22 of the electrical generator 6. The at least one stationary component 20 is a complementary component, in the electromagnetic generator, to the at least one moving component 20, namely one or more conductive coils, a magnet or a magnet/coil combination respectively. Typically the moving component 20 is one or more magnets and the stationary component 22 comprises one or more coils which surround the one or more magnets, the magnet(s) moving in an axial direction relative to the coil(s).

The expansion mechanism 18 is located on one side 24 of the at least one moving component 20 of the electrical generator 6 so that increased fluid pressure within the expansion mechanism 18 causes the at least one moving component 20 to move away from the expansion mechanism 18 in a first moving direction shown by arrow B.

A return biasing device in the form of an expansion volume 26 is provided to control the movement of the at least one moving component 20 relative to the stationary component(s) 22, as well as to provide a return force on the moving component(s) when the driving pressure in the expansion mechanism 18 is released. The expansion volume 26 typically comprises a closed body 28 containing a working fluid 30. The expansion volume 26 can be compressed by the at least one moving component 20 and thereby provide a return biasing force. The expansion volume 26 is located on the opposite side 31 of the at least one moving component 20 of the electrical generator 6 so that when the fluid pressure within the expansion mechanism 18 is reduced below a threshold, the expansion volume 26 causes the at least one moving component 20 to return back towards the expansion mechanism 18 in a second moving direction, shown by arrow C, opposite to the first moving direction. This causes the working fluid 12 to be returned to the bladder 8.

In addition to the expansion volume return force, a mechanical spring 35 can optionally be provided to provide an additional return biasing force as part of the mechanical construction of the expansion volume 26. This mechanical spring 35 can ensure that the electrical generator mechanism continues to operate (although at a lower functional capacity) in the event that the expansion volume 26 fails in its operation, for whatever reason.

The complete electrical generator 6 is contained within a magnetic shielding case 32. This prevents the host body from being subjected to undesirable magnetic fields from the electromagnetic generator.

The electrical output of the electrical generator 6 is then fed into a power/voltage regulation circuitry 34, in order to condition the output power to a suitable 'form' for use by the implant device circuitry (not shown).

In the event of a failure of any of the mechanisms or components of the electrical generator 6, an emergency back-up battery 36 is provided.

Both the power conditioning circuitry 34 and the back-up battery 36 are separate from the generator, being housed within the case 38 of the implant device 40, which may, for example, be a cardiac defibrillator or a cardiac pacemaker.

In use, the pressure bladder 8 is located within the host body on one side of a wall 42 of a circulatory vessel 44, which may be the wall of the heart or of an artery or of a vein. The pressure transmission conduit 10 extends through the wall and is sealed thereto by an annular seal 46 surrounding the pressure transmission conduit 10. The remainder of the pressure transmission conduit 10, and the assembly of the electrical generator 6, power/voltage regulation circuitry 34, back-up battery 36 and implant device 40, are disposed within the host body remote from the circulatory vessel 44. Under the influence of the pressure fluctuations of the blood circulatory system, shown by arrows D, the pressure bladder 8 is compressed and released in a predictable manner, namely a rapid pressure pulse followed by a quiescent period. This pattern follows the pressure fluctuation pattern produced by the pulsatory nature of physiological blood circulatory systems.

Figure 2:
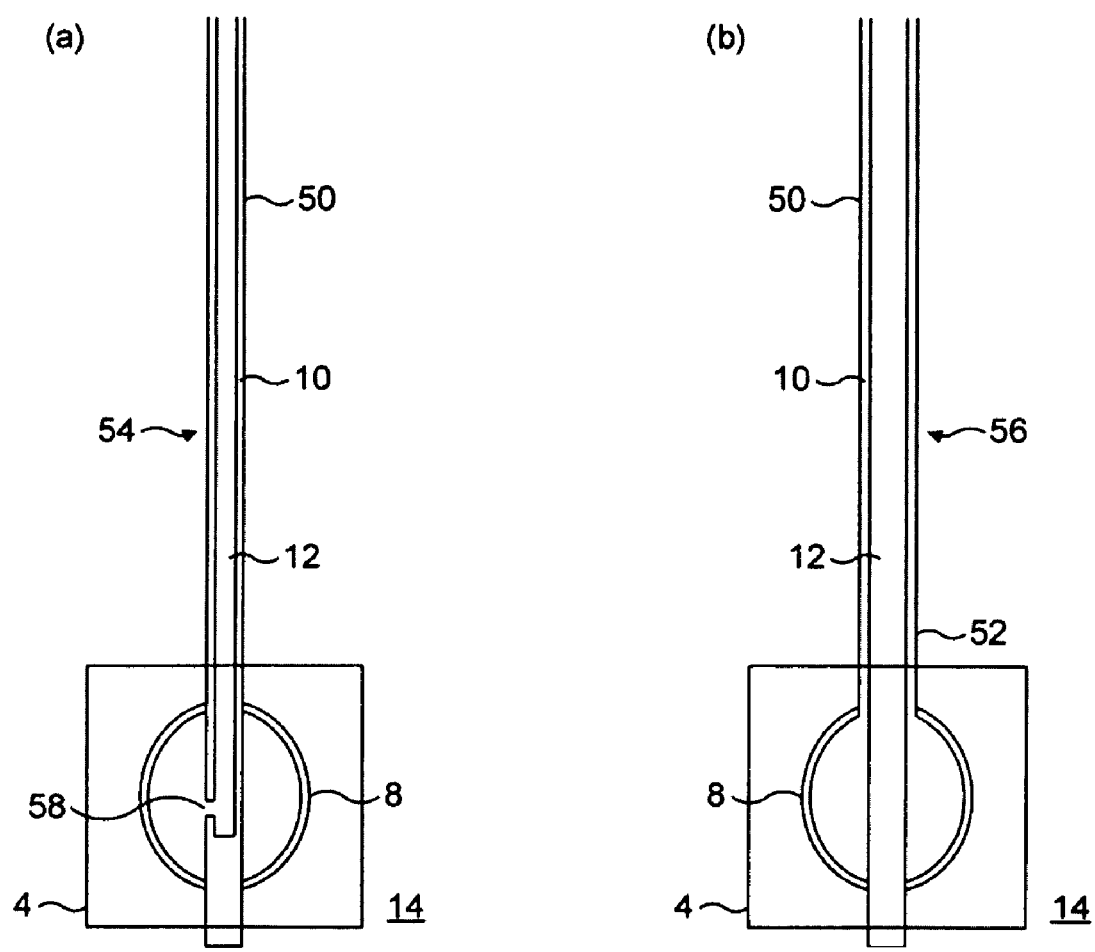
FIG. 2 is a schematic diagram of two alternative structures for a pressure responsive device, for use with the described energy harvester implant device in accordance with the described embodiment of the present invention.

Referring to FIG. 2, there is shown two apparatus for a pressure responsive device apparatus, for use with the described energy harvester implant device. These show preferred modifications to standard electrode leads, for use with the described energy harvester implant device.

The pressure responsive device 4 is located on the distal end 14 of the electrode lead 50 and is formed by a pressure bladder 8 and a pressure transmission conduit 10, filled with pressure transmission working fluid 12. In the embodiment that uses a central transmission tube 54, the standard electrode lead is modified at manufacture to increase the internal guide-tube diameter from 0.45 mm to 1 mm. A fluid passage hole 58 is provided to connect the pressure bladder 8 to the central transmission conduit 54.

In the embodiment that uses an external transmission tube, an annular transmission tube 56 is added to the outside of a standard electrode lead 50, and is protected from crushing by a helical-wound crush resistant winding 52.

In the first preferred embodiment, where the pressure bladder 8 is located within the right ventricle of the heart and the expansion mechanism 18 is located within the case 32 of the energy harvester implant device 2, the pressure experienced by the bladder 8 is expected to fluctuate from a resting value of 2-5 mmHg, up to 20-25 mmHg at full compression in 0.1 sec. The pressure then falls back to the resting pressure of 2-5 mmHg in 0.2 sec. The pressure then remains at values near to the resting value for 0.7 sec, defined as the quiescent period. These values assume a heart beat rate of 60 bpm. At higher rates, the proportion of active pressure fluctuation to quiescent period is 1:2—one third of the cycle is when the pressure fluctuates between its maximum and minimum levels, two thirds of the cycle comprises the quiescent period.

The pressure fluctuation is transmitted by the transmission working fluid 12 up the transmission conduit 10, by action of fluid movement, into the expansion mechanism 18 of the electrical generator 6. The expansion mechanism 18 extends and relaxes in response to the flow of fluid in the transmission conduit 10, so producing translational reciprocal displacement of the moving component(s) 20 of the electrical generator 6. The amount of displacement required is dependent on the generator configuration—moving coil, magnet or iron type, but typically is of the order of a few millimeters for any such constructions.

This translational reciprocal movement, with respect to the stationary component(s) 22 of the generator 6, produces electricity within the generator coils, in accordance with the Faraday principle. Typically, the electrical generator 6 is configured to produce over 70 microwatts of power at a voltage of from 3 to 6 volts. This can supply the pacemaker circuitry with sufficient power that the generator can be used as the principal power source for the pacemaker, without reliance on a battery (re-chargeable or not).

When the pressure bladder 8 is experiencing the aforementioned exerted pressure by the circulatory system, the moving component(s) 20 of the generator 6 will be moved to their position of maximum excursion within the generator 6 as the pressure within the circulatory system increases. This excursion produces a pressure increase in the expansion volume 26 of the generator 6. As the expansion volume 26 is compressed, this exerts a returning force on the moving component(s) 20, and a restoring force on the expansion mechanism 18.

As the pressure in the circulatory system falls, the pressure within the transmission conduit 12 and the expansion mechanism 18 will also fall. This produces a pressure differential between the expansion volume 26 and the pressure responsive device 4. This differential exerts a force on the moving component(s) 20 and the expansion mechanism 18, pushing both components back to their starting positions, by action of pressure equalisation between the expansion volume 26 and the expansion mechanism 18.

In a particularly preferred embodiment, the implant device to be powered by the electrical generator 6 is a cardiac pacemaker (or defibrillator) and the pressure responsive device 4 is assembled together with an electrode lead for the pacemaker (or defibrillator).

Conventionally, an electrode lead for a pacemaker (or defibrillator) is implanted, using a well-known surgical procedure, into the host human body so that the distal tip of the electrode lead is located within the distal apex of the right ventricle of the heart during use. This implantation technique employs a guide-tube, in the form of a catheter that annularly surrounds the electrode lead during implantation. The electrode lead is implanted in a manner so as the end portion of the lead extends through the heart valve of the right ventricle, to position the lead tip in such a manner to secure the tip to the distal apex of the ventricle, the lead being introduced into the circulatory system through a circulatory vessel wall, and the electrode lead is sealed to the wall by an annular seal that surrounds the lead and is sealingly fitted into the surgical opening in the vessel wall.

In accordance with one embodiment of the present invention, there is provided an assembly of the pressure responsive device and a transmission conduit that runs through the central lumen of an electrode lead of the implanted device. In accordance with another embodiment of the present invention, there is provided an assembly of the pressure responsive device and a transmission conduit that surrounds an electrode lead of the implant device.

Both these embodiments provide the significant advantage that the pressure responsive device can be inserted into the blood circulatory system using a known catheterisation technique. The electrode lead is modified to carry the pressure responsive device, but the method to implant both the lead and the pressure responsive device is the same as that employed just to implant the electrode lead.

At manufacture, the conventional pacemaker electrode lead assembly may be modified by a design change that increases the central electrode lead guide-wire tube from its current typical diameter of 0.45 mm to 1 mm diameter. Alternatively, the entire electrode lead and its associated guide-wire tube may be enclosed within an additional annular tube, for example of silicone rubber, supported internally or externally by a helical crush-resistance winding. In either modification, the larger diameter tube can be employed as the pressure transmission conduit 10 described above.

At the distal tip of the electrode lead, intended to be located within the right ventricle of the heart during use, a pressure bladder 6 is formed by means of either moulding the bladder shape into the standard silicone coating of the lead (in the case of the central transmission tube), or as a section of the enclosing annular tube. In the central transmission conduit embodiment, a connecting tube is formed through the side of the lead into the central tube, allowing passage of working fluid into the central tube from the pressure bladder.

The generator may typically be installed into the casing of the pacemaker at manufacturing, by connecting the expansion mechanism to the electrode connector block, the latter being modified to allow the transmission of working fluid from either configuration of transmission tube into the expansion mechanism. The electrical connections are also made at this time. The electrode lead of the pacemaker and the pacemaker device can then be shipped to surgical units as is presently done, or as a single unified construction ready for implantation into patients.

At implantation, the lead will be inserted into the heart through the venous system, as is presently done. In the embodiment of the invention in which the working transmission fluid is a gas, the pacemaker can be connected to the now implanted lead as is presently done. A modification to the connector block of the pacemaker would allow the surgeon to seal the connection at a point when the heart is in a resting phase of the cardiac cycle. This is to ensure that the transmission conduit/expansion mechanism is sealed when the heart is relaxed and minimal pressure is being exerted on the pressure bladder.

In the embodiment where the transmission working fluid is a liquid, an additional stage of preparation is required to prime the pressure transmission system. Before the pacemaker is connected to the electrode lead, the expansion mechanism is filled with transmission working fluid. The pacemaker can then be connected to the electrode lead as is presently done.

A 'top-up' aperture may optionally be provided in the connector block of the pacemaker, allowing the surgeon to insert a 'needle wire' (a flexible metal tube) through the length of the electrode lead to the distal tip. The transmission working fluid may then be injected into the transmission conduit, filling the conduit from the distal tip and expelling any air from the system. When full, the surgeon can remove the needle wire and seal the transmission conduit/expansion mechanism in the same manner as a gas filled system.

A pre-closure test of the assembled pacemaker system can now be performed, before the pacemaker is implanted in its final position, as is presently done.

Figure 3:
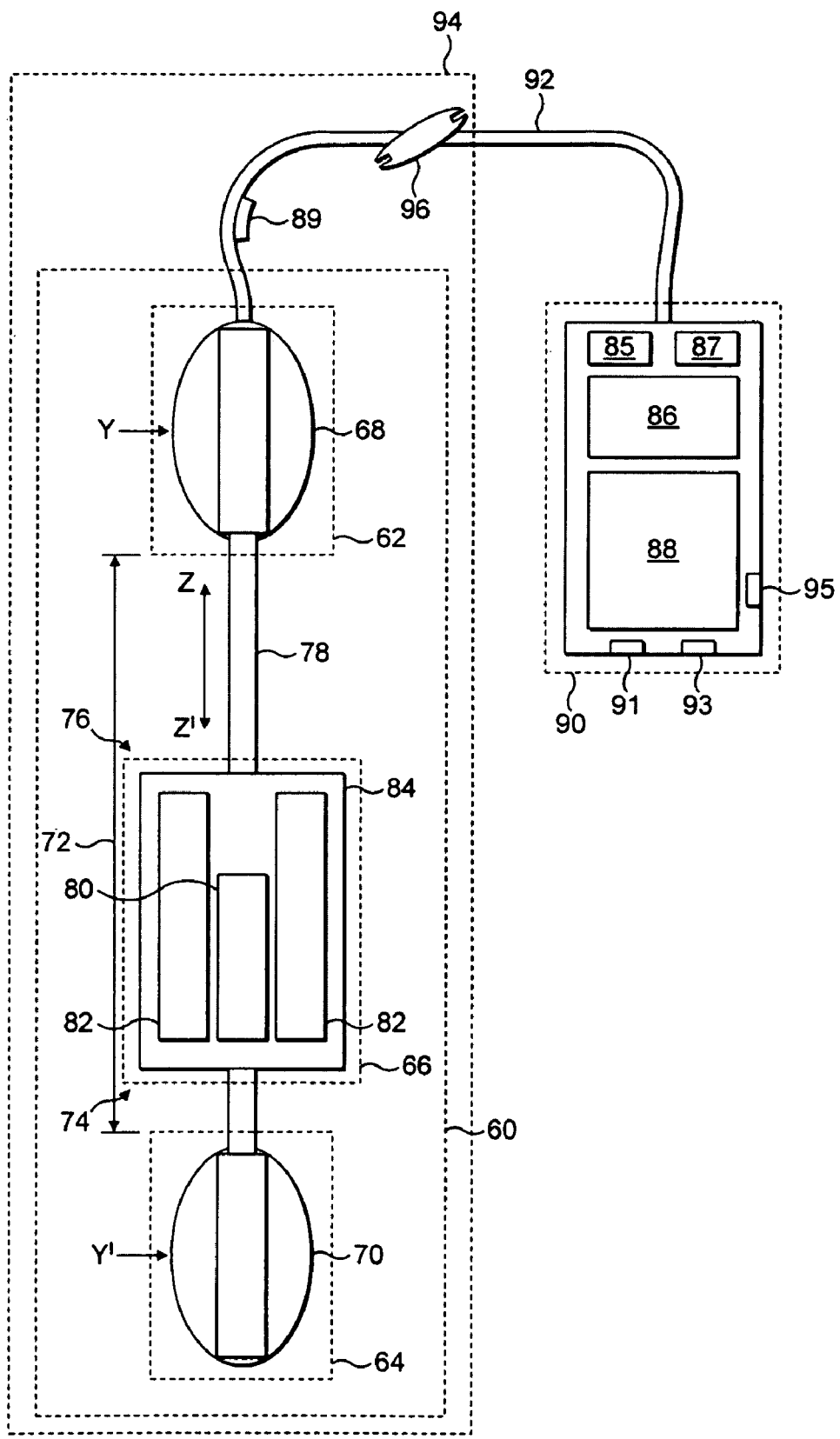
FIG. 3 is a schematic diagram of an energy harvester implant device in accordance with a second embodiment of the present invention.

Referring to FIG. 3, there is shown schematically an energy harvester implant device in accordance with a second preferred embodiment of the present invention when implanted into the human body.

The energy harvester implant device, designated generally as 60, comprises two pressure responsive devices 62, 64 containing a working fluid 78 coupled to an electrical generator 66 which converts pressure changes in the working fluid 78 into electrical energy. In use, the energy harvester implant device 60 is implanted into the living body so that the pressure responsive devices 62, 64 are subjected to pressure fluctuations (represented by arrows Y and Y') within the living body, and in particular to blood pressure fluctuations found within the blood circulatory system.

The pressure responsive devices 62, 64 comprise deformable pressure bladders 68, 70 linked together by a pressure transmission conduit 72, with the electrical generator 66 forming part of the transmission conduit 72. The pressure responsive devices 62, 64 are hydraulic or pneumatic devices, and are filled with a pressure transmitting working fluid 78 which is a biologically inert liquid or gas. The pressure bladders 68, 70, which may comprise a bellows structure, are respectively located at each end 74, 76 of the electrical generator 66, with one pressure responsive device 62 being located, in use, within the right atrium of the heart and the other pressure responsive device 64 being located, in use, in the right ventricle of the heart. The pressure transmitting working fluid 78 is caused selectively to move along the transmission conduit 72 in opposed directions, dependent on the pressure exerted on the pressure responsive devices 62, 64 by the compression cycle patterns of the heart, along the conduit 72, shown by the arrows Z and Z', and thereby to transmit the pressure fluctuations found within the circulatory system, detected by the pressure responsive devices 62, 64, to the electrical generator 66.

Such pressure fluctuations are periodic, cyclical and predictable. Therefore, in an atrial compression phase of a cardiac cycle, when the pressure bladder 68 is compressed by relatively high blood pressure within the atrium, the working fluid 78 is passed, under hydraulic or pneumatic pressure, along the conduit 72, connecting the pressure bladder 68 to the electrical generator 66. Once within the generator 66, the working fluid 78 is directed against at least one moving component 80, which operates to generate electrical power as discussed in detail below. In the ventricular compression phase of the cardiac cycle, when the blood pressure on the atrial bladder 68 is relatively low and the blood pressure on the ventricle bladder 70 is relatively high, the working fluid 78 is directed against the opposite face of at least one moving component 80, producing a return movement of the at least one moving component 80.

The at least one moving component 80 is a magnet, a conductive coil or a magnetically permeable material, which is disposed in such a position so as to be electromagnetically coupled to the at least one stationary component 82 of the electrical generator 66. The at least one stationary component 82 is a complementary component, in the electromagnetic generator, to the at least one moving component 80, namely one or more conductive coils, a magnet or a magnet/coil combination respectively. Typically the at least one moving component 80 is one or more magnets and the at least one stationary component 82 comprises one or more coils which surround the one or more magnets, the magnet(s) moving in an axial direction relative to the coil(s).

The complete electrical generator 66 is contained within a magnetic shielding case 84. This prevents the host body from being subjected to undesirable magnetic fields from the electromagnetic generator.

The electrical output of the electrical generator 66 is then fed into a power/voltage regulation circuitry 86, in order to condition the output power to a suitable 'form' for use by the implant circuitry (not shown).

In the event of a failure of any of the mechanisms or components of the electrical generator 66, an emergency back-up battery 88 is provided.

Both the power conditioning circuitry 86 and the back-up battery 88 are separate from the generator, being housed within the case 84 of the implant device 90 to be powered by the energy harvester implant device 60, which may, for example, be a cardiac defibrillator or a cardiac pacemaker. Other devices that can be powered by this harvester device 60 will be apparent to those skilled in the art.

In use, the energy harvester implant device 60 is located within the right-side chambers of the heart, with the pressure responsive devices 62, 64 being located one in the right atrium and one in the right ventricle respectively. The pressure transmission conduit 72 extends through the atrioventricular tricuspid valve of the heart and is held thereto by the form of the valves cusps surrounding the pressure transmission conduit 72. The electrical generator 66, being part of the pressure transmission conduit 72, is located within the right ventricle.

Under the influence of the pressure fluctuation of the blood circulatory system, shown by arrows Y and Y', the atrial pressure bladder 68 is compressed and released in a predictable manner, namely a rapid pressure pulse followed by a quiescent period. Shortly before the pressure fluctuation of the atrium is finished, the pressure fluctuation of the ventricle starts, acting on the ventricle pressure bladder 70. The pressure fluctuation pattern experienced by the pressure responsive devices 62, 64 (and therefore the pressure bladders 68, 70) follows the pressure fluctuation pattern produced by the pulsatory nature of physiological blood circulatory systems.

In the second preferred embodiment, when the pressure bladders 68, 70 are located within the right atrium and right ventricle of the heart respectively, the pressure experienced by the bladders is expected to fluctuate with predictable form and values. For the right atrium the pressure fluctuates from a resting value of 0-3 mmHg, up to 8-10 mmHg at full compression in 0.1 sec. The pressure then falls back to the resting pressure of 0-3 mmHg in 0.2 sec. The pressure then remains at values near to the resting value for 0.7 sec, defined as the quiescent period. For the right ventricle the pressure fluctuates from a resting value of 2-5 mmHg, up to 20-25 mmHg at full compression in 0.1 sec. The pressure then falls back to the resting pressure of 2-5 mmHg in 0.2 sec.

These values assume a heart beat rate of 60 bpm. At higher rates, the proportion of active pressure fluctuation to quiescent period is 1:2—one third of the cycle is when the pressure fluctuates between its maximum and minimum levels, two thirds of the cycle comprises the quiescent period. There is a period of pressure fluctuation overlap of the atrium and the ventricle. Typically this is in the order of 10% of the cardiac cycle times.

The pressure fluctuations are transmitted by the transmission working fluid 78 up the transmission conduit 72, by action of fluid movement, into the electrical generator 66. The at least one moving component 80 moves along within the at least one stationary component 82 in response to the flow of fluid in the transmission conduit 72, so producing translational displacement of the at least one moving component 80 of the electrical generator 66.

The amount of displacement required is dependent on the generator configuration—moving coil, magnet or iron type, but typically is of the order of a few millimeters for any such constructions of the expected size of the preferred embodiment.

This translational displacement, with respect to the at least one stationary component 82 of the generator 66, produces electricity within the generator coils, in accordance with the Faraday principle. Typically, the electrical generator 66 is configured to produce over 70 microwatts of power at a voltage of from 3 to 6 volts. This can supply the pacemaker circuitry with sufficient power that the generator can be used as the principal power source for the pacemaker, without reliance on a battery (re-chargeable or not).

During use, the atrial pressure responsive device 62, with its pressure bladder 68 experiences the aforementioned exerted pressure by atrial contraction. This exerted pressure is transmitted along the transmission conduit 72 by means of the transmission working fluid 78, to act against the at least one moving component 80. The at least one moving component 80 of the generator 66 will be moved to its/their position of maximum excursion within the generator 66 by action of fluid flow, as the pressure within the right atrium and therefore the atrial pressure bladder 68 increases. This excursion of the at least one moving component 80 pushes the transmission working fluid 78 on the opposite side of the at least one moving component 80 through the transmission conduit 72 into the ventricle pressure responsive device 64, expanding its pressure bellows 70.

As the cardiac cycle continues and the right atrial pressure falls, the right ventricle pressure starts to rise, overlapping the atrial pressure fall by approximately 10% of the cardiac cycle period. When the right ventricle pressure rises over the right atrial pressure, the pressure differential will cause the pressure bellows 70 of the ventricle pressure responsive device 64 to begin to compress. This will move the transmission working fluid 78 through the transmission conduit 72 in the opposite direction to the initial displacement of the at least one moving components 80, returning the at least one moving component 80 to its initial position within the generator 66. The cardiac cycle then enters its quiescent period before repeating its cycle.

In a particularly preferred embodiment, the implant device to be powered by the described invention is a cardiac pacemaker (or defibrillator). The complete energy harvester implant device, designated generally as 60 is pre-assembled on an application specific electrode lead 92 for the pacemaker (or defibrillator) and supplied ready to implant to appropriate surgical centres.

The complete electrode lead assembly 94 is implanted using the current conventional surgical procedure into the host human body. The lead assembly 94 is inserted and positioned so that the distal tip of the electrode lead 92 and the ventricle pressure responsive device 64 is located within the right ventricle of the heart and the atrial pressure responsive device 62 is located within the right atrium.

The electrode lead assembly 94 is implanted in a manner so the lead 92 passes through the wall of the left sub-clavian vein, along the inside wall of the left sub-clavian vein, through the superior vena cava and into the right atrium. The lead assembly 94 is positioned to place the atrial 62 and ventricular 64 pressure responsive devices in the corresponding chambers of the heart. The transmission conduit 72 is placed into a corner of the atrioventricular tricuspid valve, using the valves form to hold the transmission conduit 72 at the edge of the valves diameter.

The current conventional implantation technique employs a guide-tube, in the form of a catheter (not shown) that annularly surrounds the electrode lead assembly 94 during implantation. Using the guide tube to direct the lead assembly 94 to be implanted, the lead assembly 94 is introduced into the circulatory system through a circulatory vessel wall, typically the left sub-clavian and, on removal of the catheter guide tube, the electrode lead 92 is sealed to the wall by an annular seal 96 that surrounds the lead 92 and is sealingly fitted into the surgical opening in the vessel wall.

In FIG. 3 the energy harvester implant device 60 is shown as being elongate and linear, having a longitudinal direction of implantation corresponding to the direction Z-Z'. In order to enable the device 60 to be readily steered during implantation to the correct location within the heart, it is desired that the device 60 is provided with to rigidity against transverse deformation. For example, a facility may be provided to insert a guide stylet wire through the energy harvester implant device 60 during insertion, thereby stiffening the device in the longitudinal direction so as to resist transverse bending. The energy harvester implant device 60 may optionally be provided with a preformed curvature or non-linear shape, instead of being longitudinally straight as shown in FIG. 3, to assist device insertion, the provision of a non-linear shape being known practice for the insertion of other intra-cardiac devices). For example, the stylet may be deliberately bent so that the energy harvester implant device 60 assumes a correspondingly bent configuration which allows the device to be steered more easily. A corresponding stiffening may be provided in the energy harvester implant device 2 of the first embodiment The application uses of the preferred embodiments of the present invention are now described.

Cardiac Function Data Collection.

With the use of the pressure fluctuation patterns found within the circulatory systems of a biological body as a source of energy harvesting, access is gained to a critical aspect of the biological functioning of the circulatory system.

Recently it has been found that the pressure fluctuation patterns found within the circulatory system of humans can be used to diagnose and monitor a variety of physiological and patho-physiological conditions, examples being increased blood pressure and diabetes. However, for most abnormal cardiac conditions, currently it is necessary to introduce a percutaneous probe into the heart to record the pressure fluctuation patterns occurring to make an early and accurate diagnosis, or monitor for the progression of patho-physiological conditions effecting the heart and circulatory system.

With the need to introduce an electrode lead into the heart of pacemaker recipients and the described embodiment utilising the same pressure fluctuation patterns to produce energy, the resulting power output of the described embodiments already contains this vital information needed by diagnosticians.

The use of a pacemaker pre-determines that a diagnosis of a cardiac condition has been made, of a severity requiring an implant to control or mitigate any adverse events. What is not available to current medical practice is the long term collection of the data required to monitor the progression of these conditions. This data collection is currently limited to regular, but time limited, sessions within a hospital or clinic, where a percutaneous probe can be inserted, as described above.

With the use of a pacemaker with the described invention, access to this data can now be continuous and can be gathered and stored by appropriate data collection circuitry, as a part of the normal functioning of the pacemaker.

For example, a processor 85 and data store 87 (FIG. 3) in the implant device 90 are provided for processing a signal feed output from the energy harvester 60 that is representative of the pressure changes within the body of the mammal to determine a physiological condition of the body, and to store the resulting data. The processor 85 and/or data store 87 can be accessed from outside the body by a direct connection 91 and/or by a transmitter 93. A further connection 95 may be provided to connect the implant device 90 to other implant devices (not shown).

This gives medical professionals a data set that shows a complete activity 'log' of the patients heart function, enabling them to monitor the progression of conditions in a level of detail previously unattainable.

For example, the electrical output for diagnostic purposes provided by the signal feed output can provide the following:

a. The electrical output can provide information on right atrial and right ventricular function. Processing of this data can allow diagnostic information on the electrophysiological status of the patient at any given point in time. This should allow precise discrimination of the exact cardiac rhythm or arrhythmia that that individual is currently experiencing. This will allow more appropriate delivery of pacing or defibrillation therapies from the implanted pacemaker or cardiac defibrillator.

b. The electrical output can provide a precise assessment of the haemodynamic consequences of any change in cardiac arrhythmia. This is a key aspect in determining whether potentially painful therapy is delivered from an implantable cardiac defibrillator or withheld.

c. Acquisition of this data over time would allow trend data to be recorded which would provide a measure of disease progression and allow clinicians to objectively assess the impact of therapeutic interventions such as programming changes to the implanted device or the administration of pharmacological agents.

d. Acquisition of the data as a measure of haemodynamic status would, via predefined algorithms, allow automatic adjustment of device functionality. A reduction in amplitude of the signal obtained may initiate changes in the relative timings of right atrial, right ventricular and left ventricular stimulation. This function would be particularly relevant at the time of initial implantation of the device.

This data log can also show when and how often the pacemaker is needed to fire, in order to control the underlying condition affecting the patients' heart function, allowing a further detailed assessment of the patients' condition.

Importantly, the electrical output for diagnostic purposes provided by the signal feed output can exhibit a combined haemodynamic-rhythm perturbation which provides a unique identifier of abnormal rhythm and concurrent haemodynamic consequence. This has significant benefits for the clinician because it provides a signal representing a combination of data, which can be easily obtained over extended time periods once the implant device with the electrical generator has been implanted, and which data has hitherto only been obtainable independently by a clinician during a medical diagnosis and/or using more complicated clinical techniques.

Another aspect of having direct access to the blood circulation of the patient is the ability to embed sensors within the electrode lead, to provide continuous biochemical analysis of the patients' blood. Such a biochemical sensor 89 is shown in FIG. 3.

This contrasts with current analysis practice, where a sample must be taken from the patient, then sent to a biochemistry lab for analysis. This method restricts the level of analysis able to be conducted on a patient's blood chemistry, as it can only tell the chemical composition of a patient's blood at the time of sampling.

By having a biochemical sensor permanently within the blood stream, data regarding the fluctuations of chemical composition over time can be collected (even remotely over telecoms systems), without effort, and so a comprehensive analysis can be conducted on a data set that has far more detail than could ever be provided by conventional sampling.

Biological Physiological & Biochemical Data Collection & Monitoring.

Use of the described invention (in any of its preferred embodiments) is not limited to the pacemaker/defibrillator application mentioned in the preferred embodiments. The described invention can be used to power any medical (or non-medical) implant that requires long term power, irrespective of whether a pacemaker is required by the patient or not. Also, by having a component of the implant device within the blood stream of the patient, access is gained to the blood chemistry of the individual, allowing close monitoring of physiological and biochemical processes for extended periods of time.

By changing the pacemaker electrode lead for an alternative lead designed to carry an external connector point for other implant devices, or one designed to carry the generators power output only, a number of devices suitable for long-term implantation and data collection can be used within a biological body.

This direction of application of the described invention opens the field of in-vivo biological process monitoring, enabling health professionals to gather vital information on the long-term functioning of the physiological and biochemical processes affecting their patients. Alternative devices that could be powered by the described invention will be apparent to those skilled in the art.

Also, placement of the implant device to be powered is not restricted to the typical implantation site of a pacemaker case. With the use of micro wires, similar to those used in percutaneous neural function investigations, and using a combination of the circulatory system and subcutaneous tunnelling to route the wires to an implantation site, an implant device can be powered by the described invention anywhere in the biological body under study.

This opens the range of fields that the describe invention can be applied to, beyond biological assessment, into fields such as Functional Electronic Stimulation for patients with neuromuscular disorders, or active biochemical monitoring/dispensing devices such as Insulin Pumps for diabetics.

Also, as power requirements of electronic systems fall, more diverse applications can be considered, such as biological individual tracking using GPS transceivers for population and migration studies, or more ambitious still, for powering prosthetic/cybernetic implants, as this field grows to maturity.

The preferred embodiments of present invention can provide a device in the form of an electromagnetic generator, located within a sealed case of an implanted device, driven by pressure fluctuations found within a biological body, by means of a pressure bladder, and used as the principal energy source of an implanted device such as a cardiac defibrillator or a cardiac pacemaker. In use, the pressure bladder may be situated within the circulatory system of a human or animal body, and in particular within a cardiac region, a venous region or an arterial region of the circulatory system. The pressure bladder contains a pressure transmission fluid, for transmission of the pressure fluctuations found within the circulatory system to the electromagnetic generator. The pressure transmission fluid is a biologically inert liquid or gas. A pressure transmission tube of any suitable length, communicates pressure fluctuations from the pressure bladder to the electromagnetic generator thereby to drive the latter by pressure pulses. The pressure transmission fluid moves between the aforementioned pressure bladder and an expansion mechanism of the electromagnetic generator. The transmission tube may be the central tube of a pacemaker electrode lead. Such combined structure of the transmission tube and the pacemaker electrode lead may be assembled during manufacture of the pacemaker electrode lead, or may be assembled by retrofitting of an annular tube to a conventional pacemaker electrode lead.

Typically, in the preferred embodiments of present invention the pressure fluctuations may produce linear motion of the generator mechanism, although rotational motion may alternatively be employed. The expansion mechanism may comprise an elastically expanding volume or a non-elastically expanding volume. Preferably, the electromagnetic generator is located within the case of the implant device to be powered electrically by the electromagnetic generator. However, alternatively the electromagnetic generator may be located outside the case of the implant device, and connected thereto by flexible electrical connectors, such as electrical leads.

In the preferred embodiments of present invention the electromagnetic generator may be of the moving coil type, the moving magnet type or the moving iron type. The electromagnetic generator includes moving mechanical components which are displaced, most preferably linearly and reciprocally, by the action of the expansion mechanism. Most preferably, the electromagnetic generator is of a type that is acceptable for long-term biological implantation within a sealed implanted device such as a pacemaker or defibrillator, and can act as the primary power source for such implanted devices.

In the preferred embodiments of present invention, the expansion volume acts on the moving parts of the generator, to compensate for the change in internal volume resulting from the movement of the expansion mechanism and moving component(s) of the electromagnetic generator. The expansion volume acting on the moving parts of the generator is of such a configuration to provide pressure-matched back pressure acting in opposition to the expansion mechanism on the moving component(s) of the electromagnetic generator, to control the movement of the expansion mechanism. The expansion volume can provide a pressure-matched back pressure on the moving component(s) to provide a return force on the expansion mechanism, such that when the pressure acting on the pressure bladder is reduced, the internal pressure of the expansion volume acts to push the moving parts of the generator back to a starting position within the generator, ready for the next pressure fluctuation cycle.

In the embodiment in which two pressure-responsive devices, in the form of bladders in the illustrated embodiment of FIG. 3, are provided, each pressure-responsive device can be disposed within a respective part of the heart, for example the right atrium and the right ventricle respectively. This provides a structure that can automatically accommodate internal and external pressure changes without compromising device functionality or patient safety. For example, the provision of two opposed pressure-responsive devices, subjected in use to alternating pressure, means that excessively high pressure on one side of the electrical generator can be relieved on the low pressure side, and excessive pressures or pressure changes can be alleviated. In the event of a significant change in external pressure, such as that encountered in aircraft (particularly in the event of sudden cabin depressurisation), the body adjusts its own internal pressure and therefore by using two internal cardiac pressure sources (atrial and ventricular), each having a respective interconnected pressure-responsive device disposed therein, this readily ensures that there is not an excessively large differential pressure that could damage the apparatus and/or the patient.

In the preferred embodiments of present invention, an electronic circuit may additionally be provided which is of a type to regulate and condition the electrical output of the electromagnetic generator, for use by implanted devices. Also, an emergency back-up battery supply may be provided for unforeseen failures of the generator mechanism or components.

The preferred embodiments of the present invention provide the use of a body movement energy harvesting generator as the primary power source for Implantable Cardiac Pacemakers (ICP) applications and/or general medical use. In particular, autonomic (subconscious) initiated body movements are used to harvest energy from the human body. Such movements may comprise pressure fluctuations in the right ventricle of the human heart. The pressure bladder can harvest energy from pressure fluctuations in the right ventricle of the heart. A modified ICP electrode lead can transfer mechanical energy, by use of a working fluid, between a harvester mechanism located in right ventricle and the electrical generator mechanism. The electrical generator can be a linear electromagnetic generator. A linear expansion bellows can act as an actuator mechanism for the electrical generator. A back pressure in an expansion volume can be used to control the displacement of the actuator mechanism.

In a particularly preferred embodiment of present invention, a pacemaker houses the electrical generator.

Various modifications to the disclosed embodiments will be apparent to those skilled in the art, and such modifications are encompassed within the scope of the present invention as defined by the appended claims.

What is claimed is:

1. An implant apparatus for implantation into a mammal, the implant apparatus comprising:
   an implant device having an electrode lead for implantation into a body;
   an energy harvester comprising a pressure responsive device for containing a working fluid, and an electrical generator which is coupled to the pressure responsive device and is adapted, in use, to convert pressure changes in the working fluid into electrical energy; and
   at least one electrical connection between the electrical generator and the implant device, the electrical generator being adapted to provide electrical power to the implant device,
   wherein the electrical generator is adapted to provide a signal feed output that is sent from the electrical generator to the implant device along the at least one electrical connection, and the implant device is adapted to process the signal feed output,
   wherein the electrical generator comprises a first component that is disposed in such a position so as to be electromagnetically coupled to at least one second component of the electrical generator, the at least one second component being a complementary component, in the electrical generator, to the first component, wherein the electrical generator is adapted, in use, to direct the working fluid against a face of the first component such as to move the first component relative to the at least one second component, and wherein the first component comprises one of a magnet, a conductive coil, and a magnetically permeable material, and the second component comprises one of a conductive coil, a magnet, and a combination of a magnet and a coil, respectively.

2. An implant apparatus according to claim 1 wherein the implant device is adapted to record the signal feed output.

3. An implant apparatus according to claim 1 wherein the implant device is adapted to monitor the signal feed output.

4. An implant apparatus according to claim 1 wherein the pressure responsive device comprises a deformable pressure bladder and a pressure transmission conduit.

5. An implant apparatus according to claim 4 wherein the pressure bladder is located at one end of the pressure transmission conduit and the other end of the pressure transmission conduit is located within the electrical generator.

6. An implant apparatus according to claim 4 wherein the pressure transmission conduit is assembled together with the electrode lead.

7. An implant apparatus according to claim 6 wherein the assembly of the pressure transmission conduit and the electrode lead is adapted to be implanted into the body in a common catheterisation step.

8. An implant apparatus according to claim 1 wherein the electrode lead annularly surrounds the pressure transmission conduit.

9. An implant apparatus according to claim 8 wherein the pressure transmission conduit is capable to be used as a guide-wire tube for the electrode lead during a catheterisation step, with the electrode lead being configured to be sealingly fitted to a wall of the body or of an artery.

10. An implant apparatus according to claim 9 wherein the pressure transmission conduit annularly surrounds the electrode lead during a catheterisation step.

11. An implant apparatus according to claim 10 wherein the pressure transmission conduit is supported internally or externally by a helical crush-resistance winding.

12. A method of implanting an implant apparatus into a mammal, the method comprising the steps of:
(a) providing an implant apparatus comprising:
an implant device having an electrode lead for implantation into body;
an energy harvester comprising a pressure responsive device for containing a working fluid, and an electrical generator which is coupled to the pressure responsive device and is adapted, in use to convert pressure changes in the working fluid into electrical energy; and
at least one electrical connection between the electrical generator and the implant device, the electrical generator being adapted to provide electrical power to the implant device,
wherein the electrical generator is adapted to provide a signal feed output that is sent from the electrical generator to the implant device along the at least one electrical connection, and the implant device is adapted to process the signal feed output,
wherein the electrical generator comprises a first component that is disposed in such a position so as to be electromagnetically coupled to at least one second component of the electrical generator, the at least one second component being a complementary component, in the electrical generator, to the first component, and wherein the electrical generator is adapted, in use, to direct the working fluid against a face of the first component such as to move the first component relative to the at least one second component; and wherein the first component comprises one of a magnet, a conductive coil, and a magnetically permeable material, and the second component comprises one of a conductive coil, a magnet, and a combination of a magnet and a coil, respectively; and (b) implanting at least a part of the pressure responsive device, and the electrode lead into the body in a common catheterisation step.

13. A method according to claim 12 wherein at least a part of the pressure responsive device is assembled together with the electrode lead whereby the assembly is adapted to be implanted into the body in the common catheterisation step.

14. A method according to claim 13 wherein the pressure responsive device comprises a deformable pressure bladder and a, pressure transmission conduit, and the part of the pressure responsive device comprises at least the pressure bladder and a portion of the pressure transmission conduit.

15. A method according to claim 14 wherein the pressure bladder is located at one end of the pressure transmission conduit and the other end of the pressure transmission conduit is located within the electrical generator.

16. A method according to claim 12 wherein the pressure transmission conduit annularly surrounds the electrode lead.

17. A method according to claim 16 wherein the pressure transmission conduit is adapted to be sealingly fitted to a wall of the body or of an artery.

18. A method according to claim 16 wherein the pressure transmission conduit annularly surrounds the electrode lead during catheterisation, and is adapted to be sealingly fitted to a wall of the body or of an artery.

19. A method according to claim 18 wherein the pressure transmission conduit is supported internally or externally by a helical crush-resistance winding.

20. A method according to claim 12 wherein the implant device records the signal feed output.

21. A method according to claim 12 wherein the implant device monitors the signal feed output.

22. An implant apparatus for implantation into a mammal, the implant apparatus comprising:
an implant device having an electrode lead for implantation into a body;
an energy harvester comprising a pressure responsive device for containing a working fluid, and an electrical generator which is coupled to the pressure responsive device and is adapted, in use, to convert pressure changes in the working fluid into electrical energy; and
at least one electrical connection between the electrical generator and the implant device, the electrical generator being adapted to provide electrical power to the implant device and a signal feed output to be processed by the implant device,
wherein the electrical generator comprises a first component that is disposed in such a position so as to be electromagnetically coupled to at least one second component of the electrical generator, the at least one second component being a complementary component, in the electrical generator, to the first component, and wherein the electrical generator is adapted, in use, to direct the working fluid against a face of the first component such as to move the first component relative to the at least one second component, wherein the first component comprises one of a magnet, a conductive coil, and a magnetically permeable material, and the second component comprises one of a conductive coil, a magnet, and a combination of a magnet and a coil, respectively.

23. An implant apparatus according to claim 22 wherein the implant device is adapted to record the signal feed output.

24. An implant apparatus according to claim 22 wherein the implant device is adapted to monitor the signal feed output.

25. An implant apparatus according to claim 22 wherein the pressure responsive device comprises at least one deformable pressure bladder and a pressure transmission conduit.

26. An implant apparatus according to claim 25 wherein a first pressure bladder is located at one end of the pressure transmission conduit and a second pressure bladder is located at the other end of the pressure transmission conduit, with the electrical generator located between the pressure bladders.

27. An implant apparatus according to claim 25 wherein the electrical generator comprises part of the pressure transmission conduit.

28. An implant apparatus according to claim 25 wherein the assembly of the pressure transmission conduit and the electrode lead is adapted to be implanted into the body in a common catheterisation step.

29. An implant apparatus according to claim 22 wherein the electrode lead is constructed as part of a distal tip of an electrode lead of a cardiac device selected from a pacemaker and a defibrillator.

30. An implant apparatus according to claim 22 wherein the energy harvester is constructed as part of the distal tip of an electrode lead with a separate power output connection at the proximal end of the lead for connection of additional implant devices.

31. An implant apparatus according to claim 22 wherein the energy harvester is constructed as a distal tip of an output lead with a power output connection at the proximal end of the lead for connection of additional implant devices.

32. An implant device for implantation into a mammal, the implant device comprising:
a cardiac device having an electrode lead for implantation into a body;
a pressure responsive device for containing a working fluid, and an electrical generator which is coupled to the pressure responsive device and is adapted, in use, to convert pressure changes in the working fluid into electrical energy;
at least one electrical connection between the electrical generator and the implant device, the electrical generator being adapted to provide electrical power to the implant device and a signal feed output to be processed by the implant device; and
at least one sensor associated with the electrode lead, the at least one sensor being adapted to monitor at least one parameter of a patient's blood biochemistry,
wherein the electrical generator comprises a first component that is disposed in such a position so as to be electromagnetically coupled to at least one second component of the electrical generator, the at least one second component being a complementary component, in the electrical generator, to the first component, and
wherein the electrical generator is adapted, in use, to direct the working fluid against a face of the first component such as to move the first component relative to the at least one second component,
wherein the first component comprises one of a magnet a conductive coil, and a magnetically permeable material, and the second component comprises one of a conductive coil, a magnet, and a combination of a magnet and a coil, respectively.

33. An implant device according to claim 32 wherein the at least one sensor is embedded within a surface of the electrode lead.

34. An implant device according to claim 32 wherein the cardiac device is adapted to process the signal feed output and to store data therefrom within the cardiac device.

35. An implant device according to claim 34 wherein the cardiac device is adapted to permit the stored data to be downloaded therefrom to a remote device.

36. An implant device according to claim 32 wherein the at least one sensor is a biochemical sensor assembled together with the electrode lead.

37. An implant device according to claim 36 wherein the biochemical sensor is embedded within a material of the electrode lead.

38. An implant device according to claim 36 wherein an assembly of the biochemical sensor and the electrode lead is adapted to be implanted into the body in a common catheterisation step.

39. An implant device for implantation into a mammal, the implant device comprising:
a pressure responsive device for containing a working fluid, and an electrical generator which is coupled to the pressure responsive device and is adapted, in use, to convert pressure changes in the working fluid into electrical energy and to output a signal that is representative of pressure changes within a body of the mammal,
a cardiac device having an electrode lead for implantation into a body; and
at least one electrical connection between the electrical generator and the implant device, the electrical generator being adapted to provide electrical power to the implant device, and wherein the cardiac device is adapted to receive the signal,
wherein the electrical generator comprises a first component that is disposed in such a position so as to be electromagnetically coupled to at least one second component of the electrical generator, the at least one second component being a complementary component, in the electrical generator, to the first component, and
wherein the electrical generator is adapted, in use, to direct the working fluid against a face of the first component such as to move the first component relative to the at least one second component,
wherein the first component comprises one of a magnet, a conductive coil, and a magnetically permeable material, and the second component comprises one of a conductive coil, a magnet, and a combination of a magnet and a coil, respectively.

40. An implant device according to claim 39 wherein the cardiac device is adapted to derive and store data from the signal within the cardiac device.

41. An implant device according to claim 40 wherein the cardiac device is adapted to permit the stored data to be downloaded therefrom to a remote device.

42. A clinical apparatus comprising an implant device according to claim 39 in combination with a processor adapted to receive and process the signal to provide clinical data.

43. A clinical apparatus according to claim 42 wherein the clinical data comprises information on at least one of the right atrial and right ventricular function of the body.

44. A clinical apparatus according to claim 42 wherein the clinical data comprises information on cardiac arrhythmias.

45. A clinical apparatus according to claim 42 wherein the processor is adapted to store the clinical data over a period of time, to record trend data to provide a measure of disease progression.

46. A clinical apparatus according to claim 42 wherein the processor is adapted to provide a feedback control signal, based on the clinical data, for the implant device.

47. A method of operating an implant apparatus that is implanted into a mammal, the implant apparatus having a pressure responsive device for containing a working fluid, and an electrical generator which is coupled to the pressure responsive device and is adapted, in use, to convert pressure changes in the working fluid into electrical energy and to output a signal that is representative of pressure changes within a body of the mammal, a cardiac device having an electrode lead for implantation into a body; and at least one electrical connection between the electrical generator and the implant device, the electrical generator being adapted to provide electrical power to the implant device, and wherein the cardiac device is adapted to receive the signal, wherein the electrical generator comprises a first component that is disposed in such a position so as to be electromagnetically coupled to at least one second component of the electrical generator, the at least one second component being a complementary component, in the electrical generator, to the first component, and wherein the electrical generator is adapted, in use, to direct the working fluid against a face of the first component such as to move the first component relative to the at least one second component, wherein the first component comprises one of a magnet, a conductive coil, and a magnetically permeable material, and the second component comprises one of a conductive coil, a magnet, and a combination of a magnet and a coil, respectively; the method including:
processing a signal output from the electrical generator that is representative of the pressure changes within the body of the mammal to determine a physiological condition of the body.

48. A method according to claim 47 wherein the signal output from the electrical generator is representative of combined cardiac haemodynamic-rhythm perturbation.

49. A method according to claim 47 wherein the processing provides clinical data from the signal output.

50. A method according to claim 49 wherein the clinical data comprises information on at least one of right atrial and right ventricular function of a heart of the mammal.

51. A method according to claim 49 wherein the clinical data comprises information on cardiac arrhythmias.

52. A method according to, claim 49 wherein the processing stores the clinical data over a period of time to record trend data to provide a measure of disease progression.

53. A method according to claim 47 wherein the processing provides a feedback control signal, based on clinical data, for the implant apparatus.

54. A method according to claim 47 wherein the pressure responsive device comprises at least two pressure-deformable portions and a pressure transmission conduit therebetween.

55. A method according to claim 54 wherein a first pressure-deformable portion is located at one end of the pressure transmission conduit and a second pressure-deformable portion is located at the other end of the pressure transmission conduit, with the electrical generator located between the pressure-deformable portions.

56. A method according to claim 55 wherein each pressure-deformable portion comprises a bladder.

57. A method according to claim 55 wherein the pressure responsive device is implanted into a heart of a mammal, with the first pressure-deformable portion being locatable within a ventricle of the heart and a second pressure-deformable portion being locatable within an atrium of the heart.

58. A method according to claim 47 wherein the electrical generator is adapted to provide a signal feed output representative of pressure changes of the pressure responsive device.

59. An implant apparatus for implantation into a mammal, the implant apparatus comprising: a pressure responsive device for containing a working fluid, and an electrical generator which is coupled to the pressure responsive device and is adapted, in use, to convert pressure changes in the working fluid into electrical energy; the pressure responsive device comprising at least two pressure-deformable portions and a pressure transmission conduit therebetween,
wherein the electrical generator forms part of the transmission conduit, is located between the pressure-deformable portions, and comprises a first component that is disposed in such a position so as to be electromagnetically coupled to at least one second component of the electrical generator, the at least one second component being a complementary component, in the electrical generator, to the first component, and
wherein the electrical generator is adapted, in use, to direct the working fluid against a face of the first component such as to move the first component relative to the at least one second component, and
wherein the first component comprises one of a magnet, a conductive coil, and a magnetically permeable material, and the second component comprises one of a conductive coil, a magnet, and a combination of a magnet and a coil, respectively.

60. An implant apparatus according to claim 59 wherein a first pressure-deformable portion is located at one end of the pressure transmission conduit and a second pressure-deformable portion is located at the other end of the pressure transmission conduit.

61. An implant apparatus according to claim 60 wherein each pressure-deformable portion comprises a bladder.

62. An implant apparatus according to claim 60 wherein the pressure responsive device is adapted to be implanted into a heart of a mammal, with a first pressure-deformable portion being locatable within a ventricle of the heart and a second pressure-deformable portion being locatable within an atrium of the heart.

63. An implant apparatus according to claim 59 further comprising at least one electrical connection extending from the electrical generator, the electrical generator being adapted to provide an electrical output, by the at least one electrical connection, to an implant device.

64. An implant apparatus according to claim 63 wherein the electrical output comprises at least one of electrical power to operate the implant device and a signal feed output representative of pressure changes of the pressure responsive device.

65. An implant apparatus according to claim 64 wherein the signal feed output is representative of combined cardiac haemodynamic-rhythm perturbation.

* * * * *

UNITED STATES PATENT AND TRADEMARK OFFICE
CERTIFICATE OF CORRECTION

PATENT NO. : 8,135,469 B2
APPLICATION NO. : 12/041298
DATED : March 13, 2012
INVENTOR(S) : Stephen Roberts et al.

It is certified that error appears in the above-identified patent and that said Letters Patent is hereby corrected as shown below:

Col. 16, Claim 1, line 51, remove [[adapted, in use,]] and insert --configured-- in lieu thereof.
Col. 16, Claim 1, line 55, remove [[adapted]] and insert --configured-- in lieu thereof.
Col. 16, Claim 1, line 57, remove [[adapted]] and insert --configured-- in lieu thereof.
Col. 16, Claim 1, line 60, remove [[adapted]] and insert --configured-- in lieu thereof.
Col. 16, Claim 1, line 63, insert --movable-- between "first" and "component" and insert --linearly-- between "is" and "disposed".
Col. 16, Claim 1, lines 64 and 65, insert --stationary-- between "second" and "component" at both occurrences.
Col. 17, Claim 1, line 1, remove [[adapted, in use,]] and insert --configured-- in lieu thereof.
Col. 17, Claim 1, line 2, insert --movable-- between "first" and "component" in both occurrences.
Col. 17, Claim 1, line 3, insert --linearly-- before "relative" and insert --stationary-- between "second" and "component".
Col. 17, Claim 1, line 5, insert --one of-- after "wherein" and insert --and second-- between "first" and "component".
Col. 17, Claim 1, line 7, insert --other of the first and-- before "second".
Col. 17, Claim 1, line 9, delete ", respectively" from the end of the sentence.

Col. 17, Claim 2, line 11, remove [[adapted]] and insert --configured-- in lieu thereof.

Col. 17, Claim 3, line 13, remove [[adapted]] and insert --configured-- in lieu thereof.

Col. 17, Claim 7, line 26, remove [[adapted]] and insert --configured-- in lieu thereof.

Col. 17, Claim 12, lines 5 and 6, remove [[adapted, in use]] and insert --configured--.
Col. 17, Claim 12, line 8, remove [[adapted]] and insert --configured-- in lieu thereof.
Col. 17, Claim 12, line 10, remove [[adapted]] and insert --configured-- in lieu thereof.
Col. 17, Claim 12, line 12, remove [[adapted]] and insert --configured-- in lieu thereof.
Col. 17, Claim 12, line 13, insert --movable-- between "first" and "component" and insert --linearly-- before "disposed".

Signed and Sealed this
Fourteenth Day of August, 2012

David J. Kappos
*Director of the United States Patent and Trademark Office*

CERTIFICATE OF CORRECTION (continued)
U.S. Pat. No. 8,135,469 B2

Col. 17, Claim 12, line 15, insert --stationary-- between "second" and "component" in both occurrences.
Col. 17, Claim 12, line 16, insert --movable-- between "first" and "component".
Col. 17, Claim 12, line 18, remove [[adapted, in use,]] and insert --configured-- in lieu thereof.
Col. 17, Claim 12, line 19, insert --movable-- between "first" and "component" in both occurrences.
Col. 17, Claim 12, line 20, insert --linearly-- before "relative" and insert --stationary-- between "second" and "component".
Col. 17, Claim 12, line 21, insert --one of-- after "wherein" and --and second-- after "first" and add an --s-- to the end of "component".
Col. 17, Claim 12, line 22, insert --other of the first and-- before "second".
Col. 17, Claim 12, line 23, add an --s-- to the end of "component".
Col. 17, Claim 12, line 24, remove [[, respectively]] from the end of the sentence.

Col. 18, Claim 13, line 3, remove [[adapted]] and insert --configured-- in lieu thereof.

Col. 18, Claim 17, line 2, remove [[adapted]] and insert --configured-- in lieu thereof.

Col. 18, Claim 18, lines 2 and 3, remove [[adapted]] and insert --configured-- in lieu thereof.

Col. 18, Claim 22, line 6, remove [[adapted, in use,]] and insert --configured-- in lieu thereof.
Col. 18, Claim 22, line 9, remove [[adapted]] and insert --configured-- in lieu thereof.
Col. 18, Claim 22, line 11, insert --movable-- between "first" and "component" and insert --linearly-- before "disposed".
Col. 18, Claim 22, line 13, insert --stationary-- between "second" and "component" in both occurrences.
Col. 18, Claim 22, line 14, insert --movable-- between "first" and "component".
Col. 18, Claim 22, line 16, remove [[adapted, in use,]] and insert --configured-- in lieu thereof.
Col. 18, Claim 22, line 17, insert --movable-- between "first" and "component" in both occurrences.
Col. 18, Claim 22, line 18, insert --linearly-- before "relative" and insert --stationary-- between "second" and "component".
Col. 18, Claim 22, line 19, insert --one off-- after "wherein" and --and second-- before "first" and add an --s-- on the end of "component".
Col. 18, Claim 22, line 20, insert --other of the first and-- before "second" and add an --s-- on the end of "component".
Col. 18, Claim 22, lines 21 and 22, remove [[, respectively]] from the end of the sentence.

Col. 19, Claim 23, line 2, remove [[adapted]] and insert --configured-- in lieu thereof.

Col. 19, Claim 24, line 2, remove [[adapted]] and insert --configured-- in lieu thereof.

Col. 19, Claim 28, line 2, remove [[adapted]] and insert --configured-- in lieu thereof.

Col. 19, Claim 32, line 5, remove [[adapted, in use,]] and insert --configured-- in lieu thereof.
Col. 19, Claim 32, line 8, remove [[adapted]] and insert --configured-- in lieu thereof.
Col. 19, Claim 32, line 11, remove [[adapted]] and insert --configured-- in lieu thereof.
Col. 19, Claim 32, line 12, insert --movable-- between "first" and "component" and insert --linearly-- before "disposed".
Col. 19, Claim 32, line 14, insert --stationary-- before "component" in both occurrences.
Col. 19, Claim 32, line 15, insert --movable-- between "first" and "component".
Col. 19, Claim 32, line 17, remove [[adapted, in use,]] and insert --configured-- in lieu thereof.
Col. 19, Claim 32, line 18, insert --movable-- between "first" and "component" in both occurrences.
Col. 19, Claim 32, line 19, insert --linearly-- before "relative" and --stationary-- after "second" and insert --,-- after "component".
Col. 19, Claim 32, line 20, insert --one of-- after "wherein" and --and second-- after "first" and --s-- after "component".
Col. 19, Claim 32, line 21, insert --other of the first and-- before "second" and --s-- after "component".
Col. 19, Claim 32, lines 22 and 23, remove [[, respectively]] from the end of the sentence.

Col. 20, Claim 34, line 2, remove [[adapted]] and insert --configured-- in lieu thereof.

Col. 20, Claim 35, line 2, remove [[adapted]] and insert --configured-- in lieu thereof.

Col. 20, Claim 38, line 2, remove [[adapted]] and insert --configured-- in lieu thereof.

Col. 20, Claim 39, line 4, remove [[adapted, in use,]] and insert --configured-- in lieu thereof.
Col. 20, Claim 39, line 9, remove [[adapted]] and insert --configured-- in lieu thereof.
Col. 20, Claim 39, line 10, remove [[adapted]] and insert --configured-- in lieu thereof.
Col. 20, Claim 39, line 11, insert --movable-- between "first" and "component".
Col. 20, Claim 39, line 13, insert --stationary-- between "second" and "component" in both occurrences.
Col. 20, Claim 39, line 14, insert --movable-- between "first" and "component".
Col. 20, Claim 39, line 16, remove [[adapted, in use,]] and insert --configured-- in lieu thereof.
Col. 20, Claim 39, line 17, insert --movable-- between "first" and "component" in both occurrences.
Col. 20, Claim 39, line 18, insert --linearly-- before "relative" and --stationary-- after "second" and --,-- after "component".
Col. 20, Claim 39, line 19, insert --one of-- after "wherein" and --and second-- after "first" and --s-- after "component".
Col. 20, Claim 39, line 20, insert --other of the first and-- before "second" and --s-- after "component".
Col. 20, Claim 39, lines 21 and 22, remove [[, respectively]] from the end of the sentence.

Col. 20, Claim 40, line 2, remove [[adapted]] and insert --configured-- in lieu thereof.

Col. 20, Claim 41, line 2, remove [[adapted]] and insert --configured-- in lieu thereof.

Col. 20, Claim 42, line 2, remove [[adapted]] and insert --configured-- in lieu thereof.

Col. 21, Claim 45, line 2, remove [[adapted]] and insert --configured-- in lieu thereof.

Col. 21, Claim 46, line 2, remove [[adapted]] and insert --configured-- in lieu thereof.

Col. 21, Claim 47, line 4, remove [[adapted, in use,]] and insert --configured-- in lieu thereof.
Col. 21, Claim 47, line 8, remove [[adapted]] and insert --configured-- in lieu thereof.
Col. 21, Claim 47, line 9, remove [[adapted]] and insert --configured-- in lieu thereof.
Col. 21, Claim 47, line 10, insert --movable-- before "component" and --linearly-- before "disposed".
Col. 21, Claim 47, line 11, insert --stationary-- before "component".
Col. 21, Claim 47, line 12, insert --stationary-- before "component".
Col. 21, Claim 47, line 13, insert --movable-- before "component,".
Col. 21, Claim 47, line 14, remove [[adapted, in use,]] and insert --configured-- in lieu thereof and insert --movable-- after "first".
Col. 21, Claim 47, line 15, insert --movable-- after "first" and insert --linearly-- after "component".
Col. 21, Claim 47, line 16, insert --stationary-- after "second" and --one of-- after "wherein" and --and second-- after "first" and --s-- after "component".
Col. 21, Claim 47, line 17, insert --other of the first and-- before "second".
Col. 21, Claim 47, line 18, insert --s-- after "component".
Col. 21, Claim 47, line 19, remove [[, respectively]].

Col. 22, Claim 58, line 2, remove [[adapted]] and insert --configured-- in lieu thereof.

Col. 22, Claim 59, lines 3 and 4, remove [[adapted, in use,]] and insert --configured-- in lieu thereof.
Col. 22, Claim 59, line 8, insert --movable-- after "first".
Col. 22, Claim 59, line 9, insert --linearly-- before "disposed".
Col. 22, Claim 59, line 10, insert --stationary-- between "second" and "component" in both occurrences.
Col. 22, Claim 59, line 11, insert --movable-- between "first" and "component".
Col. 22, Claim 59, line 13, remove [[adapted, in use,]] and insert --configured-- in lieu thereof.
Col. 22, Claim 59, line 14, insert --movable-- between "first" and "component" in both occurrences.
Col. 22, Claim 59, line 15, insert --linearly-- before "relative" and insert --stationary-- before "component".
Col. 22, Claim 59, line 16, insert --one of-- after "wherein" and --and second-- after "first" and --s-- after "components".
Col. 22, Claim 59, line 17, insert --other of the first and-- before "second" and --s-- after "component".
Col. 22, Claim 59, lines 18 and 19, remove [[, respectively]] from the end of the sentence.

Col. 22, Claim 62, line 2, remove [[adapted]] and insert --configured-- in lieu thereof.

Col. 22, Claim 63, line 3, remove [[adapted]] and insert --configured-- in lieu thereof.

UNITED STATES PATENT AND TRADEMARK OFFICE
CERTIFICATE OF CORRECTION

PATENT NO.          : 8,135,469 B2                                    Page 1 of 5
APPLICATION NO.     : 12/041298
DATED               : March 13, 2012
INVENTOR(S)         : Stephen Roberts et al.

It is certified that error appears in the above-identified patent and that said Letters Patent is hereby corrected as shown below:

Col. 16, Claim 1, line 51, remove [[adapted, in use,]] and insert --configured-- in lieu thereof.
Col. 16, Claim 1, line 55, remove [[adapted]] and insert --configured-- in lieu thereof.
Col. 16, Claim 1, line 57, remove [[adapted]] and insert --configured-- in lieu thereof.
Col. 16, Claim 1, line 60, remove [[adapted]] and insert --configured-- in lieu thereof.
Col. 16, Claim 1, lines 62 and 63, insert --movable-- between "first" and "component" and insert --linearly-- between "is" and "disposed".
Col. 16, Claim 1, lines 64 and 65, insert --stationary-- between "second" and "component" at both occurrences.
Col. 17, Claim 1, line 1, remove [[adapted, in use,]] and insert --configured-- in lieu thereof.
Col. 17, Claim 1, lines 2 and 3, insert --movable-- between "first" and "component" in both occurrences.
Col. 17, Claim 1, lines 3 and 4, insert --linearly-- before "relative" and insert --stationary-- between "second" and "component".
Col. 17, Claim 1, line 5, insert --one of-- after "wherein" and insert --and second-- between "first" and "component".
Col. 17, Claim 1, line 7, insert --other of the first and-- before "second".
Col. 17, Claim 1, line 9, delete ", respectively" from the end of the sentence.

Col. 17, Claim 2, line 11, remove [[adapted]] and insert --configured-- in lieu thereof.

Col. 17, Claim 3, line 13, remove [[adapted]] and insert --configured-- in lieu thereof.

Col. 17, Claim 7, line 26, remove [[adapted]] and insert --configured-- in lieu thereof.

This certificate supersedes the Certificate of Correction issued August 14, 2012.

Signed and Sealed this
Fifteenth Day of January, 2013

David J. Kappos
*Director of the United States Patent and Trademark Office*

Col. 17, Claim 12, line 50, remove [[adapted, in use]] and insert --configured--.
Col. 17, Claim 12, line 55, remove [[adapted]] and insert --configured-- in lieu thereof.
Col. 17, Claim 12, line 57, remove [[adapted]] and insert --configured-- in lieu thereof.
Col. 17, Claim 12, line 60, remove [[adapted]] and insert --configured-- in lieu thereof.
Col. 17, Claim 12, lines 62 and 63, insert --movable-- between "first" and "component" and insert --linearly-- before "disposed".

Col. 17, Claim 12, lines 64 and 65, insert --stationary-- between "second" and "component" in both occurrences.
Col. 17, Claim 12, line 67, insert --movable-- between "first" and "component".
Col. 18, Claim 12, line 1, remove [[adapted, in use,]] and insert --configured-- in lieu thereof.
Col. 18, Claim 12, lines 2 and 3, insert --movable-- between "first" and "component" in both occurrences.
Col. 18, Claim 12, lines 3 and 4, insert --linearly-- before "relative" and insert --stationary-- between "second" and "component".
Col. 18, Claim 12, line 5, insert --one of-- after "wherein" and --and second-- after "first" and add an --s-- to the end of "component".
Col. 18, Claim 12, line 7, insert --other of the first and-- before "second".
Col. 18, Claim 12, line 7, add an --s-- to the end of "component".
Col. 18, Claim 12, line 9, remove [[, respectively]] from the end of the sentence.

Col. 18, Claim 13, line 15, remove [[adapted]] and insert --configured-- in lieu thereof.

Col. 18, Claim 17, line 29, remove [[adapted]] and insert --configured-- in lieu thereof.

Col. 18, Claim 18, line 33, remove [[adapted]] and insert --configured-- in lieu thereof.

Col. 18, Claim 22, line 49, remove [[adapted, in use,]] and insert --configured-- in lieu thereof.
Col. 18, Claim 22, line 53, remove [[adapted]] and insert --configured-- in lieu thereof.
Col. 18, Claim 22, lines 56 and 57, insert --movable-- between "first" and "component" and insert --linearly-- before "disposed".
Col. 18, Claim 22, lines 58 and 59, insert --stationary-- between "second" and "component" in both occurrences.
Col. 18, Claim 22, line 61, insert --movable-- between "first" and "component".
Col. 18, Claim 22, line 62, remove [[adapted, in use,]] and insert --configured-- in lieu thereof.
Col. 18, Claim 22, lines 63 and 64, insert --movable-- between "first" and "component" in both occurrences.
Col. 18, Claim 22, lines 64 and 65, insert --linearly-- before "relative" and insert --stationary-- between "second" and "component".
Col. 18, Claim 22, line 66, insert --one of-- after "wherein" and --and second-- before "first" and add an --s-- on the end of "component".
Col. 19, Claim 22, line 1, insert --other of the first and-- before "second" and add an --s-- on the end of "component".
Col. 19, Claim 22, line 3, remove [[, respectively]] from the end of the sentence.

Col. 19, Claim 23, line 5, remove [[adapted]] and insert --configured-- in lieu thereof.

Col. 19, Claim 24, line 7, remove [[adapted]] and insert --configured-- in lieu thereof.

Col. 19, Claim 28, line 23, remove [[adapted]] and insert --configured-- in lieu thereof.

Col. 19, Claim 32, line 45, remove [[adapted, in use,]] and insert --configured-- in lieu thereof.
Col. 19, Claim 32, line 50, remove [[adapted]] and insert --configured-- in lieu thereof.
Col. 19, Claim 32, line 54, remove [[adapted]] and insert --configured-- in lieu thereof.
Col. 19, Claim 32, lines 56 and 57, insert --movable-- between "first" and "component" and insert --linearly-- before "disposed".
Col. 19, Claim 32, lines 58 and 59, insert --stationary-- before "component" in both occurrences.
Col. 19, Claim 32, line 61, insert --movable-- between "first" and "component".
Col. 19, Claim 32, line 62, remove [[adapted, in use,]] and insert --configured-- in lieu thereof.
Col. 19, Claim 32, lines 63 and 64, insert --movable-- between "first" and "component" in both occurrences.
Col. 19, Claim 32, lines 64 and 65, insert --linearly-- before "relative" and --stationary-- after "second".
Col. 19, Claim 32, line 66, insert --one of-- after "wherein" and --and second-- after "first" and --s-- after "component".
Col. 20, Claim 32, line 1, insert --other of the first and-- before "second" and --s-- after "component".
Col. 20, Claim 32, line 3, remove [[, respectively]] from the end of the sentence.

Col. 20, Claim 34, line 8, remove [[adapted]] and insert --configured-- in lieu thereof.

Col. 20, Claim 35, line 11, remove [[adapted]] and insert --configured-- in lieu thereof.

Col. 20, Claim 38, line 21, remove [[adapted]] and insert --configured-- in lieu thereof.

Col. 20, Claim 39, line 27, remove [[adapted, in use,]] and insert --configured-- in lieu thereof.
Col. 20, Claim 39, line 35, remove [[adapted]] and insert --configured-- in lieu thereof.
Col. 20, Claim 39, line 37, remove [[adapted]] and insert --configured-- in lieu thereof.
Col. 20, Claim 39, line 38, insert --movable-- between "first" and "component".
Col. 20, Claim 39, line 39, insert --linearly-- before "disposed".
Col. 20, Claim 39, lines 40 and 41, insert --stationary-- between "second" and "component" in both occurrences.
Col. 20, Claim 39, line 43, insert --movable-- between "first" and "component".
Col. 20, Claim 39, line 44, remove [[adapted, in use,]] and insert --configured-- in lieu thereof.
Col. 20, Claim 39, lines 45 and 46, insert --movable-- between "first" and "component" in both occurrences.
Col. 20, Claim 39, lines 46 and 47, insert --linearly-- before "relative" and --stationary-- after "second" .

CERTIFICATE OF CORRECTION (continued)
U.S. Pat. No. 8,135,469 B2

Col. 20, Claim 39, line 48, insert --one of-- after "wherein" and --and second-- after "first" and --s-- after "component".
Col. 20, Claim 39, line 50, insert --other of the first and-- before "second" and --s-- after "component".
Col. 20, Claim 39, line 52, remove [[, respectively]] from the end of the sentence.

Col. 20, Claim 40, line 54, remove [[adapted]] and insert --configured-- in lieu thereof.

Col. 20, Claim 41, line 57, remove [[adapted]] and insert --configured-- in lieu thereof.

Col. 20, Claim 42, line 61, remove [[adapted]] and insert --configured-- in lieu thereof.

Col. 21, Claim 45, line 2, remove [[adapted]] and insert --configured-- in lieu thereof.

Col. 21, Claim 46, line 6, remove [[adapted]] and insert --configured-- in lieu thereof.

Col. 21, Claim 47, line 12, remove [[adapted, in use,]] and insert --configured-- in lieu thereof.
Col. 21, Claim 47, line 18, remove [[adapted]] and insert --configured-- in lieu thereof.
Col. 21, Claim 47, line 20, remove [[adapted]] and insert --configured-- in lieu thereof.
Col. 21, Claim 47, line 21, insert --movable-- before "component" and --linearly-- before "disposed".
Col. 21, Claim 47, line 23, insert --stationary-- before "component".
Col. 21, Claim 47, line 24, insert --stationary-- before "component".
Col. 21, Claim 47, line 26, insert --movable-- before "component,".
Col. 21, Claim 47, lines 26 and 27, remove [[adapted, in use,]] and insert --configured-- in lieu thereof and insert --movable-- after "first".
Col. 21, Claim 47, line 28, insert --movable-- after "first" and insert --linearly-- after "component".
Col. 21, Claim 47, line 29, insert --stationary-- after "second" and --one of-- after "wherein" and --and second-- after "first" and --s-- after "component".
Col. 21, Claim 47, line 31, insert --other of the first and-- before "second".
Col. 21, Claim 47, line 31, insert --s-- after "component".
Col. 21, Claim 47, line 33, remove [[, respectively]].

Col. 22, Claim 58, line 9, remove [[adapted]] and insert --configured-- in lieu thereof.

Col. 22, Claim 59, line 15, remove [[adapted, in use,]] and insert --configured-- in lieu thereof.
Col. 22, Claim 59, line 21, insert --movable-- after "first".
Col. 22, Claim 59, line 22, insert --linearly-- before "disposed".
Col. 22, Claim 59, lines 23 and 24, insert --stationary-- between "second" and "component" in both occurrences.
Col. 22, Claim 59, line 26, insert --movable-- between "first" and "component".
Col. 22, Claim 59, line 27, remove [[adapted, in use,]] and insert --configured-- in lieu thereof.
Col. 22, Claim 59, lines 28 and 29, insert --movable-- between "first" and "component" in both occurrences.

Col. 22, Claim 59, line 29 and 30, insert --linearly-- before "relative" and insert --stationary-- before "component".

Col. 22, Claim 59, line 31, insert --one of-- after "wherein" and --and second-- after "first" and --s-- after "components".

Col. 22, Claim 59, line 33, insert --other of the first and-- before "second" and --s-- after "component".

Col. 22, Claim 59, line 35, remove [[, respectively]] from the end of the sentence.

Col. 22, Claim 62, line 44, remove [[adapted]] and insert --configured-- in lieu thereof.

Col. 22, Claim 63, line 51, remove [[adapted]] and insert --configured-- in lieu thereof.